United States Patent [19]

Koelmel et al.

[11] Patent Number: 4,559,945
[45] Date of Patent: Dec. 24, 1985

[54] ABSORBABLE CRYSTALLINE ALKYLENE MALONATE COPOLYESTERS AND SURGICAL DEVICES THEREFROM

[75] Inventors: Donald Koelmel; Shalaby W. Shalaby, both of Lebanon, N.J.

[73] Assignee: Ethicon, Inc., Somerville, N.J.

[21] Appl. No.: 652,706

[22] Filed: Sep. 21, 1984

[51] Int. Cl.⁴ ............................................. A61L 17/00
[52] U.S. Cl. ................................. 128/335.5; 528/300; 528/354; 525/450
[58] Field of Search ...................... 128/335.5; 525/450; 528/300, 354

[56] References Cited

U.S. PATENT DOCUMENTS

| | | | |
|---|---|---|---|
| 2,683,136 | 7/1954 | Higgins | 528/354 |
| 4,139,525 | 2/1979 | Bacskai | 525/450 |
| 4,140,678 | 2/1979 | Shalaby et al. | 525/450 |
| 4,243,775 | 1/1981 | Rosersaft et al. | 128/335.5 |

*Primary Examiner*—Jacqueline V. Howard
*Attorney, Agent, or Firm*—Charles J. Metz

[57] ABSTRACT

Surgical devices such as filaments are made from a crystalline copolyester of glycolide, lactide, p-dioxanone, or mixture thereof, and poly(alkylene malonate).

14 Claims, No Drawings

ABSORBABLE CRYSTALLINE ALKYLENE MALONATE COPOLYESTERS AND SURGICAL DEVICES THEREFROM

The invention relates to crystalline copolyesters of alkylene malonate with glycolide, lactide, or p-dioxanone, and to surgical devices, especially surgical filaments, made therefrom.

BACKGROUND OF THE INVENTION

Synthetic absorbable polymers have been used to produce various surgical products such as sutures, implants, prostheses, and the like, for several years. Illustrative U.S. Patents that disclose such polymers are U.S. Pat. Nos. 3,297,033; 3,044,942; 3,371,069; 3,531,561; 3,636,956; RE 30,170 and 4,052,988.

This invention provides a new class of crystalline polymers that are absorbable and which have a good balance of physical and biological properties. In particular, the polymers, when fabricated into filaments, have excellent strength and compliance.

SUMMARY OF THE INVENTION

The crystalline copolyesters of the invention are derived from a poly(alkylene malonate) and either p-dioxanone, lactide, glycolide, or mixtures thereof. The copolyesters of the invention comprise repeating divalent units of the formulas:

(A) $-O-CO-CH_2-CO-O-$
(B) $-G-$, and at least one of the following, (C), (D), or (E):
(C) $-O-CO-CH_2-O-CH_2CH_2-$
(D) $-CH_2-CO-O-$
(E) $-CH(CH_3)-CO-O-$ wherein G represents the residue after removal of the hydroxyl groups of a dihydric alcohol, and wherein the divalent units (A), (B), (C), (D), and (E) are bonded to each other by ester groups formed by linking said units.

The crystalline copolyesters of the invention are useful in the production of medical and surgical products such as sutures, ligatures, ligating clips, pharmaceutical depot compositions, and the like.

THE PRIOR ART

Bacskai, in U.S. Pat. No. 4,139,525, discloses amorphous flexible glycolic acid terpolymers useful as hot melt adhesives, prepared by heating glycolic acid, its esters, its homopolymers, or mixtures thereof, with a glycol and a dibasic acid. Malonic acid is disclosed as one of the possible dibasic acids (col. 2, lines 66-67).

Higgins, in U.S. Pat. No. 2,683,136, discloses copolyesters prepared by reacting glycolic acid with other hydroxy-acids. Included among the other hydroxy-acids contemplated are low molecular weight condensation products of glycols and dibasic acids. While malonic acid may be within the scope of the dibasic acids contemplated by Higgins, it is not specifically disclosed. Polymers produced by reacting glycolic acid (as opposed to glycolide) with a polyester under Higgins' disclosed reaction conditions would not be expected to have a molecular weight high enough or a sufficient degree of crystallinity to be spinnable into a useful fiber.

DETAILED DESCRIPTION OF THE INVENTION

The crystalline copolyesters of the invention are produced by reacting lactide, glycolide, p-dioxanone, or mixtures thereof with a poly(alkylene malonate)polyester.

The general way to produce the poly(alkylene malonate) is to react a dihydric alcohol of the formula:

(F) $HO-G-OH$ where G has the meaning set forth above with respect to Formula (B), with a lower alkyl diester of malonic acid.

The dihydric alcohols that can be employed to produce the poly(alkylene malonate)polyesters, which can be used singly or in mixtures, include $C_2$ to $C_8$ alkylene glycols such as ethylene glycol, 1,2- and 1,3-propylene glycol, 1,4-butylene glycol, 1,6-hexylene glycol, and the like; polyalkylene glycols such as diethylene glycol, triethylene glycol, poly(oxytetramethylene)glycol, and the like; cycloaliphatic diols such as 1,4-cyclohexanedimethanol, and the like; and aromatic dihydric alcohols such as 1,4-bis(2-hydroxyethoxy)benzene, and the like. The polymethylene glycols having two to six carbon atoms are preferred. 1,3-Propylene glycol is most preferred.

It is preferred to use the malonic acid in the form of a lower alkyl diester, such as dimethyl malonate, because it is convenient to use in a transesterification reaction.

The dihydric alcohol and the malonic diester are usually reacted in proportions of from about 1.1 to about 4 moles of dihydric alcohol per mole of diester.

A catalytically effective amount of a transesterification catalyst is used in the reaction. While the reaction would proceed with a wide variety of such catalysts, as a practical matter because the copolyesters of the invention are intended for use in absorbable products, biologically acceptable catalysts used in very small amounts are preferred. Specific examples of such catalysts are stannous octoate and dibutyltin oxide. Illustrative proportions are from about 5,000 to about 50,000, and preferably about 20,000 to about 40,000, moles of malonic diester per mole of catalyst.

The preferred procedure for the preparation of the poly(alkylene malonate)polyester is illustrated by Examples 1 and 2:

EXAMPLE 1

Preparation of poly(1,3-propylene malonate)

Under a nitrogen atmosphere, the following materials were charged into a flame and vacuum dried, 300-milliliter, two-neck, round bottom flask, equipped with a vacuum tight stainless steel paddle stirrer, a short distillation head fitted with a receiver, and an adapter with a hose connection:

95.1 grams of 1,3-propanediol (1.25 moles)
0.0039 gram of dibutyltin oxide (0.000016 mole)

The flask was stoppered, purged with nitrogen, and then its contents were exposed to reduced pressure for several hours. The charged reaction vessel was next vented with nitrogen, closed off, and placed in a nitrogen atmosphere. After 80.1 grams (0.5 mole) of diethyl malonate were added to the flask, it was stoppered. The entire reaction assembly was then closed off and placed in an oil bath.

Under nitrogen at one atmosphere pressure, the reaction mixture was mechanically stirred at room temperature for 0.25 hour and subsequently subjected to the following heating schedule:

170° C. for 2.5 hours;
190° C. for 2.5 hours;
210° C. for 1.75 hours; and
230° C. for 1.75 hours.

The next day, at room temperature, the receiver containing the distillate was replaced with an empty receiver. Then, gradually over the course of 0.75 hour, the pressure in the reaction vessel was reduced to 0.05 millimeter of mercury absolute pressure. Under reduced pressure, the reaction mixture was heated according to the following heating schedule:
200° C. for 0.75 hour;
220° C. for 2.25 hours; and
230° C. for 2.0 hours.

The reaction flask was removed from the oil bath, equilibrated with nitrogen, and then allowed to cool to room temperature. The liquid polymer was isolated in a nitrogen atmosphere by first heating the reaction vessel to 60° C., and subsequently pouring the polyester product into a stainless steel beaker. The liquid polyester had an inherent viscosity ("IV") of 0.71 dl/gm, measured at 25° C. and a concentration of 0.1 gm/dl in hexafluoroisopropyl alcohol (hereinafter referred to as "HFIP").

EXAMPLE 2

Preparation of poly(1,3-propylene malonate)

Under a nitrogen atmosphere, the following materials were charged into a flame and vacuum dried, 500-milliliter, two-neck, round bottom flask, equipped with a vacuum tight stainless steel paddle stirrer, a short distillation head fitted with a receiver, and an adapter with a hose connection:
190.2 grams of 1,3-propanediol (2.5 moles)
0.0078 gram of dibutyltin oxide (0.000032 mole)

The flask was stoppered, purged with nitrogen, and then its contents were exposed to reduced pressure for several hours. The charged reaction vessel was next vented with nitrogen, closed off, and placed in a nitrogen atmosphere. 160.2 Grams (1.0 mole) of diethyl malonate was added to the flask. The flask was stoppered, and the entire reaction assembly was closed off and placed in an oil bath.

Under nitrogen at one atmosphere pressure, the reaction mixture was mechanically stirred at room temperature for 0.25 hour and subsequently subjected to the following heating schedule:
170° C. for 2.0 hours;
190° C. for 2.0 hours;
210° C. for 1.5 hours; and
230° C. for 1.5 hours.

The next day, at room temperature, the receiver containing the distillate was replaced with an empty receiver. The reaction mixture, still under nitrogen at one atmosphere pressure, was heated to 200° C. for 0.5 hour. Then the reaction vessel was closed off, and over the course of 0.75 hour, the pressure in the reaction vessel was reduced to 0.05 millimeter of mercury absolute pressure. Under reduced pressure, the reaction mixture was heated according to the following heating schedule:
220° C. for 2.0 hours; and
230° C. for 0.75 hour.

The reaction flask was removed from the oil bath, equilibrated with nitrogen, and then allowed to cool to room temperature. The liquid polymer was isolated in a nitrogen atmosphere by first heating the reaction vessel to 60° C., and subsequently pouring the polyester product into a stainless steel beaker. The liquid polyester had an inherent viscosity of 0.82 dl/gm, measured at 25° C. and a concentration of 0.1 gm/dl in HFIP.

Preparation of Copolyester

The copolyesters of the invention are produced in a coesterification reaction by reacting lactide, glycolide, p-dioxanone, or mixture thereof with a poly(alkylene malonate)polyester. The poly(alkylene malonate) used in making the copolyester will usually have an inherent viscosity of from about 0.3 to about 1.2 dl/gm, measured at 25° C. and a concentration of 0.1 gm/dl in HFIP. For convenience, the lactide, glycolide, p-dioxanone, or mixture thereof will be referred to herein as "monomer", even though lactide and glycolide are actually cyclic dimers formed by condensing two molecules of the hydroxyacid.

The co-esterification reaction is preferably carried out by dissolving the poly(alkylene malonate) in monomer, and then subjecting the reaction mixture to elevated temperature for a period of time sufficient to produce the copolyester of the invention. An additional esterification catalyst system may be added for this second polymerization, or the initial catalyst that remains in the reaction mixture from the preparation of the poly(alkylene malonate) may be sufficient to catalyze the reaction.

Typically, the copolyester will contain from about 59 to 99 weight percent, and preferably (for suture applications) from 65 to 90 weight percent, of polymerized lactic acid, glycolic acid, and/or p-dioxanone. Routine experimentation will suffice to determine the proportions of poly(alkylene malonate) and monomer that should be used in particular cases to achieve the desired proportion in the copolyester product. The Examples below illustrate typical percent conversions of monomer. The copolyesters of the invention will typically have inherent viscosities of from about 0.8 to about 2.4, and preferably from about 1 to about 1.8 dl/gm, measured at 25° C. and a concentration of 0.1 gm/dl in HFIP. The copolyesters of the invention will also typically have a minimum of about 15 percent crystallinity, and preferably at least about 20 percent crystallinity, measured by X-ray diffraction.

The following Examples 3–6 illustrate the preparation of the copolyesters:

EXAMPLE 3

Preparation of Copolyester of Glycolide and Polyester of 1,3-propanediol and Malonic Acid Under a nitrogen atmosphere at 60° C., 10.7 grams of the poly(trimethylene malonate) of Example 1 were poured into a dry 100-milliliter resin kettle. The contents of the resin kettle were then thoroughly dried by exposure to high vacuum (less than 0.05 millimeter of mercury pressure) for several hours at room temperature, followed by heating at 100° C. for 48 hours under high vacuum.

Under a nitrogen atmosphere at room temperature, 25.0 grams (0.216 mole) of glycolide were next added to the dried contents of the resin kettle. A flame dried, vacuum tight, stainless steel paddle stirrer and glass adapter with a gas port were attached to the charged reaction vessel, and the pressure in the reaction assembly was subsequently reduced to a low level for several hours. The reaction vessel was then purged with nitrogen, closed off, and placed in an oil bath. Under nitrogen at one atmosphere pressure, the reaction mixture was heated, with initially rapid mechanical stirring to facilitate dissolution of the polyester in the monomer, according to the following temperature/time sequence:

100° C. for 0.5 hour.
120° C. for 0.5 hour;
140° C. for 0.5 hour;
160° C. for 0.5 hour; and
200° C. for 5.0 hours.

(The stirring rate was slowed as the viscosity of the polymerizing mass increased.)

The resulting copolyester was isolated by first chilling the resin kettle in liquid nitrogen to separate the product from the kettle's glass walls, followed by breaking the reaction vessel, and finally collecting the frozen copolyester. While the product was still frozen, any glass still adhering to the copolyester was removed with an emery wheel. The glass-free frozen copolyester was then ground and subsequently dried at room temperature for 16 hours by exposure to vacuum. The ground product was then heated to 110° C. and a pressure of 0.05 millimeter of mercury for 16 hours to remove unreacted glycolide from the desired copolyester product; a 5.5 percent weight loss was observed. The resulting copolyester product had an inherent viscosity of 0.99 dl/gm, measured at 25° C. and a concentration of 0.1 gm/dl in HFIP, and a melting point of 198°-200° C. (by thermal microscopy).

EXAMPLE 4

Preparation of Copolyester of Glycolide and Polyester of 1,3-propanediol and Malonic Acid Under a nitrogen atosphere at 60° C., 18.7 grams of the poly(trimethylene malonate) of Example 1 were poured into a dry 250-milliliter round bottom flask. The contents of the flask were then thoroughly dried by exposure to high vacuum (less than 0.05 millimeter of mercury pressure) for several hours at room temperature, followed by heating at 110° C. for 17 hours under high vacuum.

Under a nitrogen atmosphere at room temperature, 43.6 grams (0.376 mole) of glycolide were next added to the dried contents of the flask. A flame dried, vacuum tight, stainless steel paddle stirrer and glass adapter with a gas port were attached to the charged reaction vessel, and the pressure in the reaction assembly was subsequently reduced to a low level for several hours. The reaction vessel was then purged with nitrogen, closed off, and placed in an oil bath. Under nitrogen at one atmosphere pressure, the reaction mixture was heated, with initially rapid mechanical stirring to facilitate dissolution of the polyester in the monomer, according to the following temperature/time sequence:

100° C. for 0.5 hour; and
205° C. for 5.0 hours.

(The stirring rate was slowed as the viscosity of the polymerizing mass increased.)

The resulting copolyester was isolated as described above and then ground and subsequently dried at room temperature for 16 hours by exposure to vacuum. The ground product was then heated to 120° C. and a pressure of 0.05 millimeter of mercury for 14 hours to remove unreacted glycolide from the desired copolyester product; a 2.4 percent weight loss was observed. The resulting copolyester product had an inherent viscosity of 0.92 dl/gm, measured at 25° C. and a concentration of 0.1 gm/dl in HFIP, a melting point of 168°-180° C. (by thermal microscopy), and a crystallinity of 38 percent (by X-ray diffraction).

EXAMPLE 5

Preparation of Copolyester of Glycolide and Polyester of 1,3-propanediol and Malonic Acid Under a nitrogen atmosphere at 60° C., 33.1 grams of the poly(trimethylene malonate) of Example 2 were poured into a dry 500-milliliter round bottom flask. The contents of the flask were then thoroughly dried by exposure to vacuum (less than 0.5 millimeter of mercury pressure) for 20 hours at room temperature, followed by heating at 110° C. for 20 hours under vacuum.

Under a nitrogen atmosphere at room temperature, 77.2 grams (0.666 mole) of glycolide were next added to the dried contents of the flask. A flame dried, vacuum tight, stainless steel paddle stirrer and glass adapter with a gas port were attached to the charged reaction vessel, and the pressure in the reaction assembly was subsequently reduced to a low level for several hours. The reaction vessel was then purged with nitrogen, closed off, and placed in an oil bath. Under nitrogen at one atmosphere pressure, the reaction mixture was heated, with initially rapid mechanical stirring to facilitate dissolution of the polyester in the monomer, according to the following temperature/time sequence:

100° C. for 0.66 hour; and
205° C. for 5.0 hours.

(The stirring rate was slowed as the viscosity of the polymerizing mass increased.)

The resulting copolyester was isolated as described above and then ground and subsequently dried at room temperature for 16 hours by exposure to vacuum. The ground product was then heated to 120° C. and a pressure of 0.05 millimeter of mercury for 15 hours to remove unreacted glycolide from the desired copolyester product; a 1.9 percent weight loss was observed. The resulting copolyester product had an inherent viscosity of 1.09 dl/gm, measured at 25° C. and a concentration of 0.1 gm/dl in HFIP, a melting point of 178°-185° C. (by Fisher-Johns), and a crystallinity of 37 percent (by X-ray diffraction).

EXAMPLE 6

Preparation of Copolyester of p-Dioxanone and Polyester of 1,3-propanediol and Malonic Acid Under a nitrogen atmosphere at 60° C., 8.4 grams of the poly(trimethylene malonate) of Example 2 were poured into a dry 250-milliliter round bottom flask. The contents of the flask were then thoroughly dried by exposure to vacuum (less than 0.05 millimeter of mercury pressure) for several hours at room temperature, followed by heating at 110° C. for 18 hours under vacuum.

Under a nitrogen atmosphere at room temperature, 47.6 grams (0.466 mole) of p-dioxanone ("PDO") and 0.00628 gram of stannous octoate ($1.55 \times 10^{-5}$ mole) were next added to the dried contents of the flask. (The stannous octoate was added as a solution in toluene.) A flame dried, vacuum tight, stainless steel paddle stirrer and glass adapter with a gas port were attached to the charged reaction vessel, and the pressure in the reaction assembly was subsequently reduced to a low level for several hours. The reaction vessel was then purged with nitrogen, closed off, and placed in an oil bath. Under nitrogen at one atmosphere pressure, the reaction mixture was heated, with initially rapid mechanical stirring to facilitate dissolution of the polyester in the monomer, according to the following temperature/time sequence;
75° C. for 0.5 hour; and
100° C. for 8.5 hours.
(The stirring rate was slowed as the viscosity of the polymerizing mass increased.)

The resulting copolyester was isolated as described above, ground, and subsequently dried at room temperature for 16 hours by exposure to vacuum. The ground product was then heated to 80° C. and a pressure of 0.05 millimeter of mercury for 52 hours to remove unreacted p-dioxanone from the copolyester product; a 22.8 percent weight loss was observed. The resulting copolyester product had an inherent viscosity of 1.97 dl/gm, measured at 25° C. and a concentration of 0.1 gm/dl in HFIP, a melting point of 99°–104° C. (by thermal microscopy), and a crystallinity of 38 percent (by X-ray diffraction).

EXTRUSION

The copolyesters are melt extruded through a spinnerette in a conventional manner to form one or more filaments.

Extrusion of the copolyesters described herein was accomplished using an INSTRON Capillary Rheometer. The copolymers were packed in the preheated (90° to 150° C.) extrusion chamber and extruded through a 40 mil die (L/D=24.1) after a dwell time of 9 to 11 minutes at the extrusion temperature and a ram speed of 2 cm/min. While extrusion temperatures depend both on the polymer Tm and on the melt viscosity of the material at a given temperature, extrusion of the subject copolyesters at temperatures of about 10° to 75° C. above the Tm is usually satisfactory. The extrusion temperatures of the example copolyesters described herein ranged from 190° to 200° C. The extrudate was taken up through an ice water quench bath at either 24 or 40 feet/minute. A screw-type extruder or similar device can be substituted for the INSTRON Capillary Rheometer.

The extrudate filaments are subsequently drawn about 4× to 7× in a one or multistage drawing process in order to achieve molecular orientation and improve tensile properties. The extrudates described herein were drawn 2 hours to about 1 week after extrusion. (The length of time elapsed between extrusion and drawing may affect the drawing process because the extrudate may need time to develop sufficient crystallinity to facilitate orientation; the optimum time elapsed is easily determined by simple experimentation for each fiber composition.) The manner of drawing is as follows:

The extrudate (diameter range, 13–20 mils) is passed through rollers at an input speed of four feet per minute and into a heated draw bath of glycerine. The temperatures of the draw bath can vary from about 25° to 90° C.; the examples described herein employ temperatures between 44° and 65° C. The draw ratio in this first stage of drawing can vary from 3× to about 7×; the examples described herein employ draw ratios from 4× to 5×. The partially drawn fibers are then placed over a second set of rollers into a glycerine bath (second stage) kept at temperatures ranging from 50° to 95° C.; the examples described herein employ second stage draw temperatures of 69° to 75° C. Draw ratios of up to 2× are applied in this second stage, but a ratio of up to 1.375× has been employed in the examples. The fiber is passed through a water-wash, taken up on a spool, and dried. A set of hot rollers can be substituted for a portion or all of the glycerine draw bath. The resulting oriented filaments have good straight and dry tensile strengths.

Dimensional stability and tensile strength retention of the oriented filaments may be enhanced by subjecting the filaments to an annealing treatment. This optional treatment consists of heating the drawn filaments to a temperature of from about 40° to 130° C., most preferably from about 60° to 110° C. while restraining the filaments to prevent any substantial shrinkage. This process may begin with the filaments initially under tension or with up to 20% shrinkage allowed prior to restraint. The filaments are held at the annealing temperature for a few minutes to several days or longer depending on the temperature and processing conditions. In general, annealing at 60° to 110° C. for up to about 24 hours is satisfactory for the copolyesters of the invention. Optimum annealing time and temperature for maximum fiber in vivo strength retention and dimensional stability is readily determined by simple experimentation for each fiber composition.

The characteristic properties of the filaments of the invention are readily determined by conventional test procedures. The tensile properties (i.e. straight and knot tensile strengths, Young's Modulus, and elongation) displayed herein were determined with an INSTRON tensile tester. The settings used to determine the straight tensile, knot tensile, break elongation, and Young's Modulus were the following, unless indicated:

|  | Gauge Length (cm) | Chart Speed (cm/min) | Crosshead Speed (cm/min) |
|---|---|---|---|
| Straight Tensile | 12 | 20 | 10 |
| Knot Tensile | 5 | 10 | 10 |
| Break Elongation | 12 | 20 | 10 |
| Young's Modulus | 12 | 20 | 10 |

The straight tensile strength is calculated by dividing the force to break by the initial cross-sectional area of the fiber. The elongation to break is read directly from the stress-strain curve of the sample allotting 4 1/6% per centimeter of horizontal displacement.

Young's Modulus is calculated from the slope of the stress-strain curve of the sample in the linear elastic region as follows:

$$\text{Young's Modulus} = \frac{\tan \theta \times GL \times CS \times SL}{XH \times XS}$$

$\theta$ is the angle between the slope and the horizontal, XS is the initial cross-sectional area of the fiber, SL is the scale load, XH is the crosshead speed, CS is the chart speed, and GL is the gage length. The SL may be selected to provide a $\theta$ close to 45°.

The knot tensile strength of a fiber is determined in separate experiments. The test article is tied into a surgeon's knot with one turn of the filament around flexible tubing of ¼ inch inside diameter and 1/16 inch wall thickness. The surgeon's knot is a square knot in which the free end is first passed twice, instead of once, through the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

In the tables below, the extrusion, orientation, and annealing conditions, and subsequent properties of the fibers made from the copolyesters of Examples 3 to 6, are displayed.

With respect to the fibers that were sterilized by exposure to cobalt-60, the annealed monofilaments were cut to appropriate lengths, placed in individual paper folders and heat-sealable vented foil envelopes. The foil envelopes were subjected to 50° C. and 0.1 mm Hg pressure for 72 hours and subsequently sealed under nitrogen. The packaged fibers were sterilized by exposure to 2.5M rads of gamma radiation from a cobalt-60 source.

GENERATION OF ABSORPTION DATA

Under aseptic conditions, two 2-centimeter segments of a suture sample are implanted into the left and right gluteal muscles of female Long-Evans rats. Two rats per period are implanted for each of the examination periods. The animals utilized in these studies are handled and maintained in accordance with the requirements for the Animal Laboratory Welfare Act and its 1970 Amendment. The rats are killed at the appropriate periods by carbon dioxide asphyxiation, then their gluteal muscles are excised and fixed in buffered formalin. Utilizing standard histologic techniques, H and E stained slides of the muscles and implanted sutures are prepared for miscroscopic examination. Utilizing an ocular micrometer, the approximate suture cross-sectional area is estimated in each site. The cross-sectional area at five days is used as the reference value for estimating percent cross-sectional area remaining at subsequent intervals.

TABLE I
EXTRUSION, ORIENTATION CONDITIONS, AND SUBSEQUENT FIBER PROPERTIES OF GLYCOLIDE/PROPYLENE MALONATE COPOLYMERS

| Example No. of Copolyester | Example No. of Fiber | Calculated[1] Weight Comp. (G/PM) | EXTRUSION Shear Rate (Sec$^{-1}$) | Temp (°C.) | $\eta$APP[2] (Poise) | ORIENTATION 1st Stage (X/°C.) | 2nd Stage (X/°C.) | UNANNEALED FIBER PROPERTIES DIA (Mil) | Knot (PSI) | Str. (PSI) | Elong. (%) | Y.M. (PSI) |
|---|---|---|---|---|---|---|---|---|---|---|---|---|
| 3 | 7 | 68.8/31.2 | 212.6 | 200 | 1770 | 4/60 | — | 7.6 | 27550 | 52200 | 110 | 64500 |
| 3 | 8 | " | " | " | " | 4/65 | 1.25/70 | 7.3 | 36800 | 40400 | 34.2 | 69000 |
| 4 | 9 | 69.5/30.5 | 212.6 | 190 | 940 | 4/53 | 1.25/70 | 6.6 | 33499 | 38400 | 36.4 | 98500 |
| 5 | 10 | 69.6/30.4 | 212.6 | 190 | 1610 | 5X/50 | 1.2/71 | 7.7 | 53400 | 72850 | 39 | 119400 |
| 5 | 11 | " | " | " | " | 5X/52 | 1.3/75 | 7.8 | 47700 | 72250 | 44 | 148900 |
| 5 | 12 | " | " | " | " | 5X/44 | 1.2/69 | 7.8 | 51300 | 74700 | 47 | 96150 |

[1]Weight composition, glycolide/propylene malonate.
[2]Viscosity of melt.

TABLE II
EXTRUSION, ORIENTATION CONDITIONS, AND SUBSEQUENT FIBER PROPERTIES OF A PDO/PROPYLENE MALONATE COPOLYMER

| Example No. of Copolyester | Example No. of Fiber | Calculated Weight Comp. (PDO/PM) | EXTRUSION Shear Rate (Sec$^{-1}$) | Temp (°C.) | $\eta$APP (Poise) | ORIENTATION 1st Stage (X/°C.) | 2nd Stage (X/°C.) | UNANNEALED FIBER PROPERTIES DIA (Mil) | Knot (PSI) | Str. (PSI) | Elong. (%) | Y.M. (PSI) |
|---|---|---|---|---|---|---|---|---|---|---|---|---|
| 6 | 13 | 81.4/18.6 | 212.6 | 195 | 4080 | 4/53 | 1.375/75 | 8.1 | 35901 | 62300 | 59 | 89650 |

TABLE III
GLYCOLIDE/PROPYLENE MALONATE FIBER PROPERTIES BEFORE AND AFTER STERILIZATION

| Example No. of Fiber | BEFORE[1] Dia. (Mil) | Knot (PSI) | Str. (PSI) | Elong. (%) | Y.M. (PSI) | Fiber IV | Sterilization Type | AFTER Dia. (Mil) | Knot (PSI) | Str. (PSI) | Elong. (%) | Y.M. (PSI) | Fiber IV |
|---|---|---|---|---|---|---|---|---|---|---|---|---|---|
| 7 | 8.7 | — | 33850 | 46 | 90900 | 1.08 | Co$^{60}$ | 7.2 | — | 43100 | 33 | 108600 | 1.25 |
| 11 | 7.7 | 28900 | 65900 | 27 | 167000 | 0.92 | Co$^{60}$ | 7.9 | 23800 | 58500 | 26 | 170100 | 1.04 |
| 10 | 7.6 | 32900 | 63700 | 20 | 163000 | 0.94 | E.O. | 7.8 | 29100 | 61850 | 24 | 189000 | 0.85 |

[1]Example 7 fibers were annealed at 97° C. for 6.5 hours under nitrogen with 50–70 grams tension/fiber (no relaxation). Examples 10 and 11 fibers were annealed at 100° C. under nitrogen for 6.75 hours with 50–70 grams tension (no relaxation).

TABLE IV
PDO/PROPYLENE MALONATE FIBER PROPERTIES BEFORE AND AFTER STERILIZATION

| Example No. | BEFORE[2] Dia. (Mil) | Knot (PSI) | Str. (PSI) | Elong. (%) | Y.M. (PSI) | Fiber IV | Sterilization Type | AFTER Dia. (Mil) | Knot (PSI) | Str. (PSI) | Elong. (%) | Y.M. (PSI) | Fiber IV |
|---|---|---|---|---|---|---|---|---|---|---|---|---|---|
| 13 | 8.1 | 37800 | 57000 | 51 | 104000 | 1.74 | Co$^{60}$ | 7.9 | 41200 | 54700 | 52 | 123500 | 1.56 |
| 13 | 8.0 | 43800 | 59400 | 47 | 98000 | 1.68 | E.O. | 8.0 | 42000 | 58800 | 54 | 108000 | 1.75 |

[2]Example 13 fibers annealed at 82° C. under nitrogen for 6.25 hours with 5% relaxation.

BREAKING STRENGTH RETENTION

The breaking strength retention (BSR) of a fiber is determined by implanting two strands of the fiber in the dorsal subcutis of each of a number of Long-Evans rats. The number of rats used is a function of the number of implantation periods, employing 4 rats per period giving a total of eight (8) examples for each of the periods. Thus 16, 24, or 32 segments of each fiber are implated corresponding to two, three, or four implantation periods. The periods of in vivo residence are 7, 14, 21, or 28 days. The ratio of the mean value of 8 determinations of the breaking strength (determined with an INSTRON Tensile tester employing the following settings: a gage length of 1 inch, a chart speed of 1 inch/minute, and a crosshead speed of 1 inch/minute) at each period to the mean value (of 8 determinations) obtained for the fiber prior to implantation constitutes its breaking strength retention for that period.

The results of the BSR tests for the packaged and sterilized monofilament of Examples 8, 10, 11, and 13 are displayed in Tables V and VI.

The results of the in vivo absorbtion evaluations of the fibers from Examples 8, 10, and 11 are displayed below in Table V:

TABLE V

| | | | | | | | | | | | |
|---|---|---|---|---|---|---|---|---|---|---|---|
| IN VIVO DATA FOR GLYCOLIDE/PROPYLENE MALONATE MONOFILAMENTS ||||||||||||
| Example No. | Dia. (Mil) | Sterilized Fiber IV | Initial Strength (Lbs.) | Sterilization Type | % BSR ||| Absorption (% Fiber Area Remaining) |||
| | | | | | 14 | 21 | 28 days | 5 | 70 | 91 days |
| 8 | 7.3 | — | 2.05 | $Co^{60}$ | 27 | 3 | — | 100 | 2.5 | 0 |
| 10 | 7.8 | 0.85 | 2.92 | EO | 53 | 14 | — | 100 | 1 | 0 |
| 11 | 7.9 | 1.04 | 2.87 | $Co^{60}$ | — | 0.4 | 0 | | | |

TABLE IV

| | | | | | | | |
|---|---|---|---|---|---|---|---|
| IN VIVO DATA FOR PDO/PROPYLENE MALONATE MONOFILAMENTS ||||||||
| Example No. | Dia. (Mil) | Sterilized Fiber IV | Initial Strength (Lbs.) | Sterilization Type | % BSR |||
| | | | | | 21 | 28 | 42 days |
| 13 | 8.1 | 1.56 | 2.47 | $Co^{60}$ | 50 | 40 | 25 |
| 13 | 8.0 | 1.75 | 3.06 | E.O. | 78 | 79 | 53 |

What is claimed is:

1. A surgical filament comprising a drawn and oriented copolyester comprising repeating divalent units of the formulas:
   (A) —O—CO—$CH_2$—CO—O—
   (B) —G—, and at least one of the following (C), (D), or (E):
   (C) —O—CO—$CH_2$—O—$CH_2CH_2$—
   (D) —$CH_2$—CO—O—
   (E) —CH($CH_3$)—CO—O—
   wherein G represents the residue after removal of the hydroxyl groups of a dihydric alcohol, and wherein the divalent units (A) through (E) are bonded to each other by ester groups formed by linking said units.

2. The surgical filament of claim 1 wherein G represents polymethylene of from 2 to 6 carbon atoms.

3. The surgical filament of claim 1 wherein the copolyester is a copolyester of glycolide and poly(1,3-propylene malonate).

4. The surgical filament of claim 1 wherein the copolyester is a copolyester of p-dioxanone and poly(1,3-propylene malonate).

5. The surgical filament of claim 1 in sterile condition and having at least one end thereof attached to a surgical needle.

6. The surgical filament of claim 2 in sterile condition and having at least one end thereof attached to a surgical needle.

7. The surgical filament of claim 3 in sterile condition and having at least one end thereof attached to a surgical needle.

8. The surgical filament of claim 4 in sterile condition and having at lest one end thereof attached to a surgical needle.

9. A crystalline copolyester comprising repeating divalent units of the formulas:
   (A) —O—CO—$CH_2$—CO—O—
   (B) —G—, and at least one of the following (C), (D), or (E):
   (C) —O—CO—$CH_2$—O—$CH_2CH_2$—.
   (D) —$CH_2$—CO—O—
   (E) —CH($CH_3$)—CO—O—
   wherein G represents the residue after removal of the hydroxyl groups of a dihydric alcohol, and wherein the divalent units (A) through (E) are bonded to each other by ester groups formed by linking said units.

10. The copolyester of claim 9 wherein G represents polymethylene of from 2 to 6 carbon atoms.

11. The copolyester of claim 9 comprising a copolyester of glycolide and poly(alkylene malonate).

12. The copolyester of claim 9 comprising a copolyester of p-dioxanone and poly(alkylene malonate).

13. A medical or surgical device comprising the crystalline copolyester of claim 9.

14. A pharmaceutical depot composition comprising the crystalline copolyester of claim 9.

* * * * *